United States Patent [19]

Maynard

[11] Patent Number: 5,385,539
[45] Date of Patent: Jan. 31, 1995

[54] APPARATUS FOR MONITORING HEMATOCRIT LEVELS OF BLOOD

[75] Inventor: David L. Maynard, The Woodlands, Tex.

[73] Assignee: Advanced Haemotechnologies, The Woodlands, Tex.

[21] Appl. No.: 906,926

[22] Filed: Jun. 30, 1992

[51] Int. Cl.[6] ............................................. A61B 5/00
[52] U.S. Cl. ...................... 604/4; 128/632; 609/6
[58] Field of Search ............... 356/39, 40, 41; 250/338.1, 345; 128/632, 633, 634; 604/4, 5, 6

[56] References Cited

U.S. PATENT DOCUMENTS

| | | | |
|---|---|---|---|
| H1,114 | 12/1992 | Schweitzer et al. | 128/633 X |
| 4,243,883 | 1/1981 | Schwarzmann | 250/343 |
| 4,266,021 | 5/1981 | Nylen et al. | 128/632 X |
| 4,417,812 | 11/1983 | Cserey et al. | 356/435 X |
| 4,444,498 | 4/1984 | Heinemann | 356/246 |
| 4,447,150 | 5/1984 | Heinemann | 356/41 |
| 4,745,279 | 5/1988 | Karkar et al. | 250/343 |
| 4,776,340 | 10/1988 | Moran et al. | 128/624 |
| 4,880,304 | 11/1989 | Jaeb et al. | 128/633 X |
| 5,104,623 | 4/1992 | Miller | 128/633 X |
| 5,178,603 | 1/1993 | Prince | 604/6 |
| 5,188,108 | 2/1993 | Selker | 356/41 X |

FOREIGN PATENT DOCUMENTS 0286142  10/1988  European Pat. Off. .............. 356/41

OTHER PUBLICATIONS

R. J. Jendrucko et al., "The Measurement of Blood flowing in Glass Capillaries by Microphotometry[1]", *Microvascular Research*, vol. 6, pp. 316–331 (1973).

Joseph M. Schmitt et al., "New Methods for Whole Blood Oximetry", *Annals of Biomedical Engineering*, vol. 14, pp. 35–52 (1986).

J. M. Steinke et al., "Reflectance Measurements of Hematocrit and Oxyhemoglobin Saturation", *The American Physiological Society*, vol. H, pp. 147–153 (1987).

3M HealthCare Brochure, "The CDI TM 100 Hematocrit/Oxygen Saturation Monitoring System" (obtained in Sep. 1992).

Medtronic Brochure, "The MX2 TM Oxygen Saturation and Hematocrit System" (1992).

Cobe Brochure, "SAT/HCT Fiber Optic Probe" (May, 1991).

*Primary Examiner*—Sam Rimell
*Attorney, Agent, or Firm*—Workman, Nydegger & Seeley

[57] ABSTRACT

An apparatus and method are provided for measuring the hematocrit level of blood. The presently preferred embodiment comprises a light emitting device which emits an amount of light into a blood sample. This light travels through the blood sample to two light detecting devices positioned relative to the light emitting device in a predetermined geometry such that light emitted from the light emitting device must travel farther to reach one of the light detecting devices than to reach the other, thereby forming a light path from the light emitting device to one light detecting device which is longer than the path from the light emitting device to the other light detecting device. According to the present invention, the amount of light detected by one of the light detecting devices is regulated so that the amount of light detected is constant. Thereafter, the amount of light detected by the unregulated light detecting device is a linear representation of the hematocrit of the blood in the blood sample. The hematocrit sensor may be used within a plasma separator apparatus wherein the hematocrit measurement regulates the operating parameters of the autotransfusion system to maintain the hematocrit of the blood within a predetermined range.

25 Claims, 9 Drawing Sheets

APPARATUS FOR MONITORING HEMATOCRIT LEVELS OF BLOOD

BACKGROUND OF THE INVENTION

1. Technical Field

The present invention relates to apparatus and methods used in measuring and monitoring the hematocrit of blood. More specifically the present invention relates to apparatus and methods for measuring the hematocrit of blood by differential geometry and using the hematocrit measuring apparatus to automatically control the parameters of an autotransfusion system.

2. Background Information

Most surgical procedures result in some loss of blood from associated surgical incisions. Injured patients can often experience external and internal bleeding. If blood loss from injury or surgery is substantial, it becomes necessary to replenish lost blood through transfusion.

In many instances, it is possible to collect a patient's blood for use in replacing most or even all of the blood losses. It will be readily appreciated that blood collected from a wound or a surgical site will contain tissue fragments, lysed blood cells, and other unwanted substances. Such blood must be treated for removal of unwanted substances before it is safe for reinfusion into the patient.

The general procedure of collecting a patient's blood, cleansing it, and then returning it to the patient is sometimes referred to as autotransfusion. Where autotransfusion fusion is possible, it is a strongly preferred way of replacing a patient's blood losses. One reason that autotransfusion is so preferred is that it avoids incompatibility problems which sometimes can occur when giving transfusions of blood obtained from someone other than the patient. Use of a patient's own blood to replace blood losses has also become increasingly important in view of issues relating to the safety of replacement blood, such as the prevalence of acquired immune deficiency syndrome (AIDS) or other diseases among blood donors in some locales. Because of these benefits, and others, autotransfusion is often the method of choice for minimizing loss of cellular blood components during diverse procedures ranging from surgery to plasma exchange therapy, and is likely to become increasingly important in the future.

The process of removing blood plasma and other unwanted substances without any cleansing of the blood is commonly referred to as plasmapheresis. Plasmapheresis has long been practiced through use of filters having a pore size large enough to pass plasma and other unwanted substances found in the blood, such as anticoagulant, toxins and components of lysed cells (which, for purposes of brevity and simplicity, shall sometimes hereinafter be referred to collectively as the "waste components" of blood), but small enough to retain intact cells, such as red blood cells, white blood cells and platelets (which shall sometimes hereinafter be referred to collectively as the "cellular components" of blood). Plasmapheresis has also been practiced through use of a centrifuge to separate plasma and other suspended waste components from the denser cellular components, and then removing the plasma and associated waste components.

Simple removal of plasma and associated waste components is not adequate to remove all waste materials associated with blood. It has been found that a more thorough cleansing of blood can occur if the cellular components are washed after the plasma is removed. U.S. Pat. No. 4,631,050 describes a process of autotransfusion utilizing a membrane for filtration to separate waste components from cellular components. That patent describes an initial filtration to remove gross debris, followed by addition of a washing solution to reconstitute the blood, and then subjecting the reconstituted mixture to another filtration step in order to remove remaining waste components. U.S. Pat. No. 4,935,002 describes another autotransfusion apparatus for collecting, processing, and returning blood to a patient during or after surgery. The blood is filtered, washed, and separated from gross particulate refuse.

During the processing of blood for autotransfusion, it is desirable that the hematocrit of the processed blood be maintained in an appropriate range in order to obtain a thorough cleaning while minimizing problems such as clogging the filtration apparatus, damage to the cells, introducing excess solution into the patient, and the other like problems. It is believed that an appropriate range is from about 30% to 55%.

Differential geometry light transmission is a common method for measuring hematocrit. Typically, a number of emitters (especially from LEDs) and detectors are arranged in a predetermined geometric relationship. Light of a known value is emitted and the amount of light received along a given path is measured. These measurements are then applied mathematically to determine the desired parameter.

Unfortunately, while much progress has been achieved in this area, the full nature of light transmission and diffusion through blood under all circumstances has not been completely discovered, and thus is still unclear. Therefore, the mathematical equations used by the devices and methods today are based upon empirical observation by the users of what appears to work well. Consequently, such equations tend to be extremely complicated and require micro-computers to be implemented.

Additionally, after passing through the blood, the light signals received are highly non-linear before conversion, and so require high accuracy Analog/Digital converters, electrical devices used for converting analog signals to discrete digital signals, in order to analyze the wide dynamic range of values encountered by the light detectors.

Further, in the devices used today, it is difficult to precisely control the amount of light actually emitted, especially since the intensity of light output versus drive current degrades as an LED ages.

With regard to the plasma and waste separators in use today, there is no way of continuously measuring the hematocrit of the blood during processing so that the parameters of the processing system can be adjusted to compensate for hematocrit readings outside of a desired range. Therefore, the plasma and waste separators cannot be operated at their optimum levels.

SUMMARY OF THE INVENTION

It is a primary object of the present invention to provide an apparatus and method for measuring the hematocrit of blood which are simple and without need of complex equations to analyze the results.

Another object of the present invention is to provide apparatus and method for measuring the hematocrit of blood in which high accuracy Analog to Digital (A/D) converters are not needed in order to produce the linear relationship between the light output of the device and the hematocrit measurement, as is needed in many previous devices.

Yet another object of the present invention is to provide apparatus and method for optimizing use of an apparatus for effecting the cleansing of blood to remove unwanted waste materials so that it is suitable for infusion into a patient, wherein before infusion into the patient, the hematocrit is measured, thereby testing and ensuring the highest quality of blood being infused.

An additional object of the present invention is to provide apparatus and method for use with cleansing apparatus, such as a plasma separator apparatus, for effecting the cleansing of blood to remove unwanted waste materials, wherein the hematocrit of the cleansed blood is continuously monitored so that if the hematocrit measurement falls out of a prescribed range, a compensating action within the plasma separator apparatus will occur to correct for the unsuitable hematocrit level in the blood.

Additional objects and advantages of the invention are set forth hereinbelow in the detailed description, or will be appreciated by the practice of the invention.

To achieve the foregoing objects, and in accordance with the invention as embodied and broadly described herein, a hematocrit sensor apparatus is provided which is capable of measuring the hematocrit level of blood in a simple, uncomplicated manner.

More specifically, the present invention provides an apparatus and method for measuring the hematocrit level of blood which has been cleansed and processed for reinfusion into a patient by a plasma separator apparatus. The hematocrit sensor operates to continuously monitor the hematocrit level of the processed blood so that the hematocrit can be kept within a prescribed range. When the level gets too low, a microprocessor adjusts the parameter of the plasma separator apparatus in order to compensate for the low hematocrit level.

The presently preferred embodiment is a hematocrit measurement sensor comprising a light emitting device for emitting light into a blood sample and two light detecting devices for detecting the light emitted into the blood sample. The light emitting and light detecting devices are arranged in a predetermined geometric pattern such that light traveling from the light emitting device must travel further to reach one light detecting device than to reach the other light detecting device, thereby forming a light path from the light emitting device to one light detecting device which is longer than the light path from the light emitting device to the other light detecting device. The term "path" can be considered to mean generally a straight line path. However, it should be noted that there will be some amount of light scattering as the light passes through the blood. Therefore, the "path" is a composite of the light passing from the light emitting device to the light detecting device.

According to the present invention, the amount of light being received by one of the light detecting devices is regulated to be a constant value. This regulation occurs through a feedback circuit wherein the light received by one of the light detecting devices is sent through the feedback circuit to a regulation circuit which compares the received light to a constant reference source and adjusts the drive current to the light emitting device so that the value received by the regulated light detecting device matches the reference value, thereby also regulating the output of the light emitting device.

When one of the light detecting devices is regulated in this way, the output of the remaining light detecting device takes on an inherently linear representation of hematocrit. No complicated equations are necessary to transform the data generated by the light detecting device into a value for a hematocrit measurement.

Calibration then converts the already linear representation into more familiar and readable units.

The hematocrit sensor of the present invention is especially useful in combination with a plasma and waste separator system such as, for example, that used in an autotransfusion system. Although many different plasma and waste separator systems may be combined with the hematocrit sensor, the present discussion will mainly describe one system in particular. In this particular system, the hematocrit sensor is attached to the plasma separator system at output area where the processed blood is ready to be reinfused into a patient. A microprocessor may be used to connect the hematocrit sensor to the operations of the plasma separator apparatus. Limit switches may also be used.

The hematocrit sensor continuously monitors the hematocrit level of the processed blood. If the hematocrit level falls out of a certain range (here a preferred range is about 45-55%), an algorithm programmed into the microprocessor automatically adjusts the parameters of the plasma separator apparatus to compensate for the too high or too low hematocrit. For example, if the hematocrit level is too low, the microprocessor may, as one option, automatically adjust the rotor speed of the plasma separator in order to increase agitation of the blood and separation of plasma and waste from the blood. If the hematocrit level is too high, a separate action will be automatically taken to compensate for the level. Through this process, the blood being reinfused into a patient will always have an appropriate hematocrit level.

BRIEF DESCRIPTION OF THE DRAWINGS

In the accompanying drawings, which represent the best mode presently contemplated for carrying out the present invention.

DETAILED DESCRIPTION OF THE PREFERRED EMBODIMENT

The present invention is directed to a hematocrit sensor apparatus and method for measuring the hematocrit level of blood. The hematocrit sensor is especially useful in combination with a plasma separator apparatus wherein blood is processed for use in autotransfusion. However, it should also be appreciated that the teachings herein will be readily transferable to other applications involving the measurement of the hematocrit level of blood.

Figure 1:
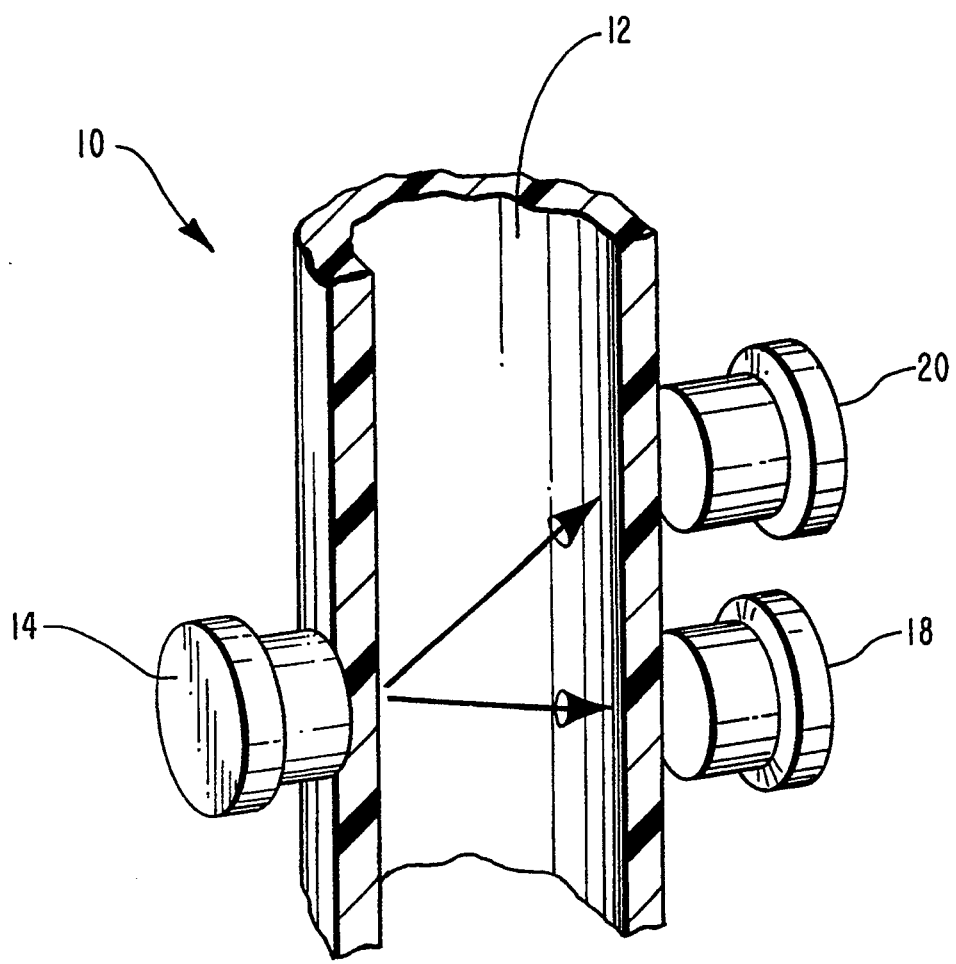
FIG. 1 is a perspective view of one embodiment of the present invention representative of "through" geometry.

Reference is first made to FIG. 1, which illustrates one embodiment of the hematocrit sensor apparatus of the present invention. In FIG. 1, the hematocrit sensor, identified generally by reference numeral 10, is positioned beside a blood sample 12. The blood sample 12 is typically held in a plastic material forming an extracorporeal circuit through which blood is passed. The hematocrit sensor 10 is configured such that the hematocrit level of a flowing bloodstream can be measured by emitting light from one side of the blood stream, through the blood, and to light detectors on the other side of the blood stream. This embodiment is referred to as "through" geometry.

A light emitting means for emitting light into a blood sample is positioned on one side of the blood sample. It should be noted that the best results occur when the thickness of the blood sample is around one millimeter. In FIG. 1, the light emitting means is illustrated as an infrared light emitting diode 14 (hereinafter "LED"). In the preferred embodiment, the LED 14 emits light at 805 nanometers. However, the light emitting means within the scope of the invention may comprise any infrared diode, or any device that emits light in the infrared range, such as a laser.

Positioned across the blood sample from LED 14 are a first light detecting means for detecting light emitted from the light emitting means and a second light detecting means for detecting light emitted from the light emitting means.

The first light detecting means is positioned to receive light emitted from the light emitting means into the blood sample along a first path to the first light detecting means. Signals put out by the first light detecting means corresponds to the amount of light detected.

The second light detecting means is positioned to receive light emitted from the light emitting means into the blood sample such that light emitted from the light emitting means must travel farther to reach the second light detecting means than to reach the first light detecting means, thereby forming a second path from the light emitting means to the second light detecting means which is longer than the first path from the light emitting means to the first light detecting means. Signals put out by the second light detecting means correspond to the amount of light detected.

In FIG. 1, these light detecting means are illustrated by a first diode 18 and a second diode 20. First diode 18 and second diode 20 are positioned to detect light emitted from LED 14 into the blood sample. Signals thereafter output by the first diode 18 and the second diode 20 correspond to the amount of light detected. Although in the preferred embodiment PIN diodes are used, any quality photodetector would be sufficient for use as the light detecting means.

In the present invention, positioning of the first and second diodes, 18 and 20, and the LED 14, is important to create the "through" geometry. LED 14 is positioned such that the path of light from LED 14 through blood sample 12 and to first diode 18 is shorter than the path of light from LED 14 through blood sample 12 and to second diode 20. Thus, by specific positioning of LED 14 and first and second diodes, 18 and 20, there is formed a short first path and a long second path.

It should be noted that correct positioning of the devices may vary with respect to distances between LED 14 and first and second diodes, 18 and 20. In the preferred embodiment, the long second path is two millimeters and the short first path is one millimeter. It has also been found successful, for example, to have a long second path two and one half millimeters and a short first path one millimeter, or to have a long second path three millimeters, and a short first path two millimeters. It appears that it is the difference in the path lengths and not particularly the magnitude of that difference that is important to the present invention. The path lengths may be adjusted. However, it is important to note that the farther away the detectors are placed from the emitters, the more power would be needed for the emitters to emit an amount of light which will reach the detectors.

Although it can be appreciated that many alternate configurations are available, one preferred configuration for forming this "through" geometry embodiment is to place first and second diodes, 18 and 20, beside each other on one side the blood sample. LED 14 is then placed on the opposite side of the blood sample along a center line between the two diodes, and then offset longitudinally toward one diode and away from the other. The side to which LED 14 is offset forms the short first path, and the remaining side forms the long second path. In FIG. 1, the path to first diode 18 is the short first path, while the path to second diode 20 is the long second path.

As discussed, light emitted from LED 14 through the blood sample is detected by first diode 18 and second diode 20. According to the present invention, it is necessary to regulate the amount of light detected on one path so that the amount detected remains a constant. The device within the scope of the present invention further comprises regulating means for regulating the intensity of light emitted by the light emitting means such that the received light on one of the paths remains at a constant value.

Another feature of the present invention are amplifying means for performing offset and gain calibration of the signals output from the light detecting means. An amplification signal is provided which is a linear representation of the hematocrit of blood in the blood sample. Within the scope of the present invention, one amplifying means is an offset and gain calibration amplifier.

Figure 2:
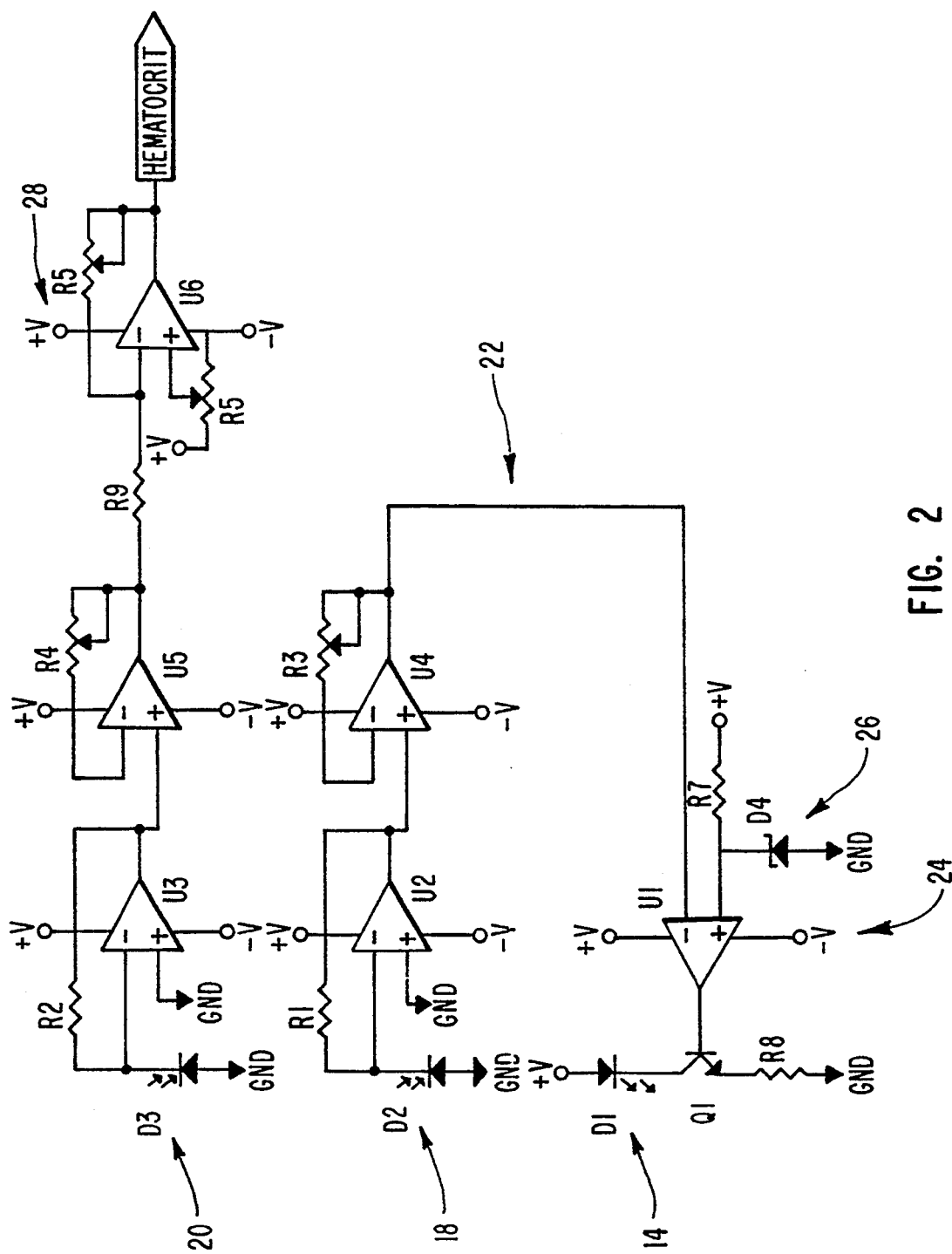
FIG. 2 is a schematic representation of "through" geometry.

In the "through" geometry, the amount of light detected on the short first path is regulated by electrically connecting first diode 18 to LED 14 through a feedback circuit. This feedback circuit is illustrated in FIG. 2 and generally labeled 22. When LED 14 is energized, light is emitted into the blood. The light received by the first diode 18 is amplified and sent through feedback circuit 22 to a regulation circuit 24. At the regulation circuit 24, the received light is compared to a constant reference source 26, and the drive current to the light emitting device is adjusted so that the value received by first diode 18 matches the value of the reference source 26, thereby regulating the output of the light emitting device and ensuring that the amount of light received by the first diode 14 remains at a constant value.

Once light received on the short first path is regulated, the amount of light received on the long path is then analyzed. Second diode 20 of the long second path outputs a signal corresponding to the amount of light it receives. The resulting output has been found to provide a linear representation of hematocrit. Additionally, it has been found that the output signal of this second diode 20 decreases as the hematocrit rises. This light is amplified and then fed to a standard "offset and gain" calibration amplifier known in the art and labelled generally in FIG. 2 as 28.

It is important to note that in devices in use today where hematocrit is measured by light detecting diodes which detect light emitted into the blood from light emitting diodes, the output signals of the light detecting diodes cannot be easily analyzed. Complex equations must be used in order to analyze and form the data into a linear hematocrit reading. Microprocessors and A/D converters are necessary to obtain the hematocrit measurements.

Figure 3:
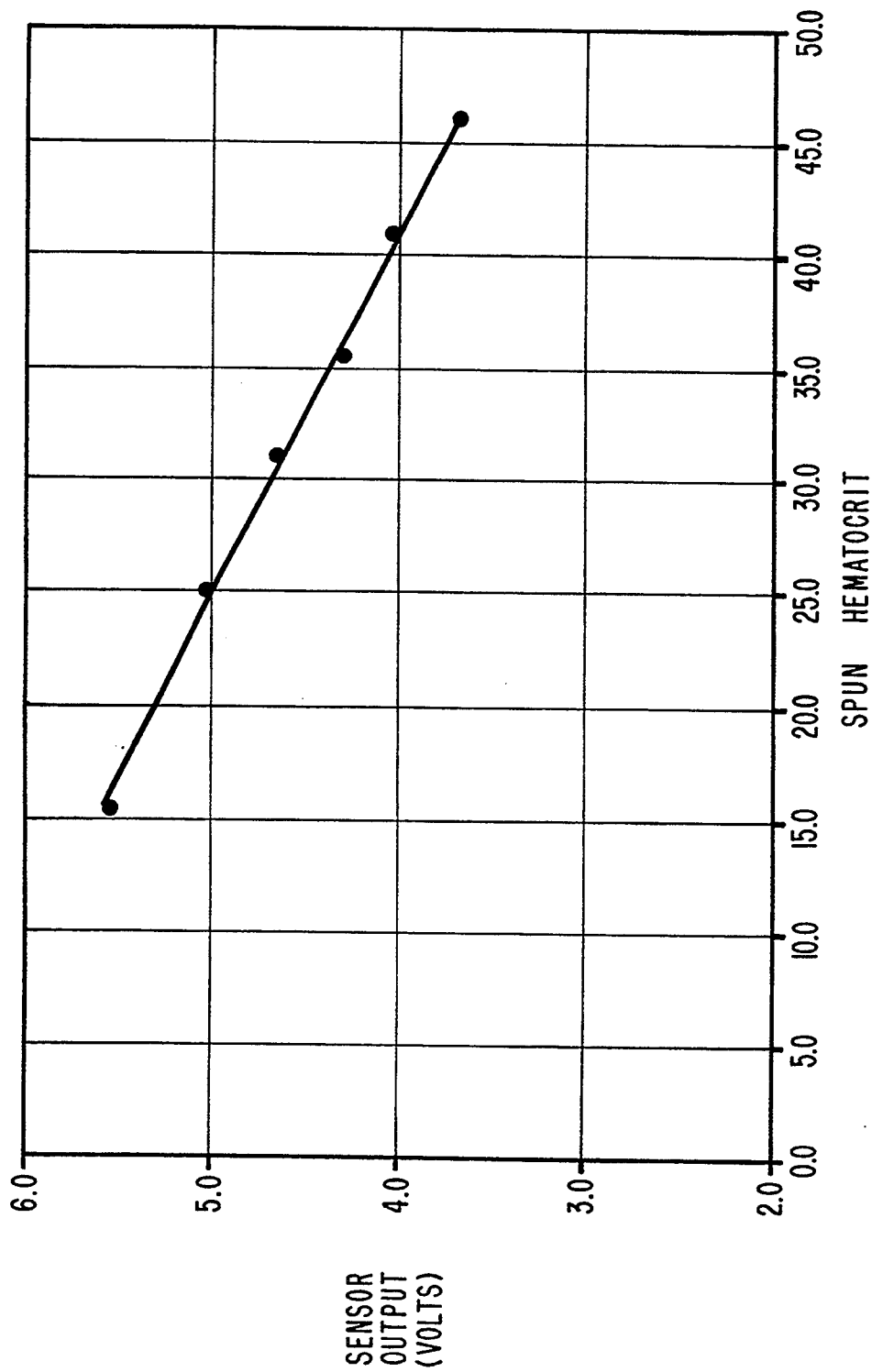
FIG. 3 is a graph of linearity found using the "through" geometry before calibration.

In contrast, with the embodiment of the present invention, when the amount of light traveling on one path is regulated, the output from the unregulated path, without the need of complex mathematical process, forms a linear hematocrit reading. FIG. 3 illustrates the linearity of the output from the "through" geometry.

Figure 4:
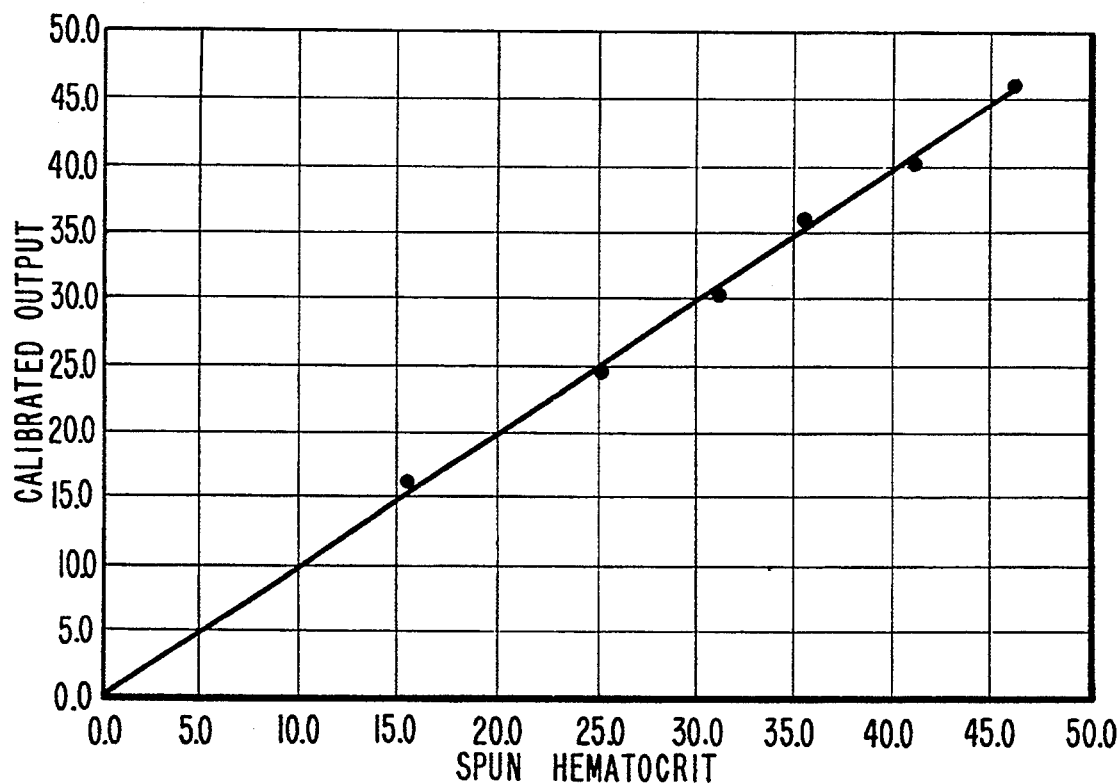
FIG. 4 is a graph of linearity found using the "through" geometry after calibration.

Calibration of the output then converts the already linear representation into more familiar and readable units. FIG. 4 illustrates the linearity of the output from the "through" geometry after calibration.

Although the "through" geometry is successful and demonstrates the practicality of the present invention, there are some limitations to the embodiment. For example, blood is a relatively dense optical medium. Therefore, the blood flow channels which are used with the "through" geometry must be very narrow in order to allow adequate light levels to penetrate. This can be undesirable due to the nature of the extracorporeal flow rates expected. A narrow flow channel was too confining.

Therefore, a second and preferred embodiment was developed. This embodiment, illustrated in FIG. 5 comprises a "back-scatter" geometry. Here, an LED 30 is positioned on the same side of the blood sample as the light detecting means, as opposed to being positioned on the opposite side as with the "through" geometry. The light detecting means are illustrated in FIG. 4 as a short path diode 32 and a long path diode 34. Again, the path to diode 34 is longer than the path to diode 32. As the light emitted into the blood stream does not have to fully penetrate the blood stream for detection by the light detecting means to occur, the thickness of the blood flow channel is not at issue. It is important to note that the back-scatter path is not a simple path. The back-scattered light detected is not simply one path of light, but more of an aggregation of light reflected back through the blood. FIG. 4 presents a simplified illustration of a back-scattered light path.

In the "back-scatter" geometry, the long second path is regulated so that the amount of light detected remains at a constant value. (Recall that in the "through" geometry, the short first path is regulated.) The long path diode 34 is electronically connected to LED 30 by a feedback circuit, illustrated in FIG. 6 and labelled generally as 42. The amount of light detected by long path diode 34 is amplified and fed to a regulation circuit 44. This circuit then compares the light received by the long path diode 34 to a constant reference source 46 and adjusts the drive current to LED 30 so that the value received on the long second path matches the value of constant reference source 46. As with the "through" geometry, this holds constant the amount of light received by one path.

The signal is then fed to a standard "offset and gain" calibration amplifier 48. The resulting output is the linear hematocrit representation. In the back-scatter geometry, as the hematocrit rises, the output signal of the short first path increases. By contrast, it should be noted that in the "through" geometry, the situation is reverse. There, as the hematocrit rises, the output signal of the long second path decreases.

Figure 6:
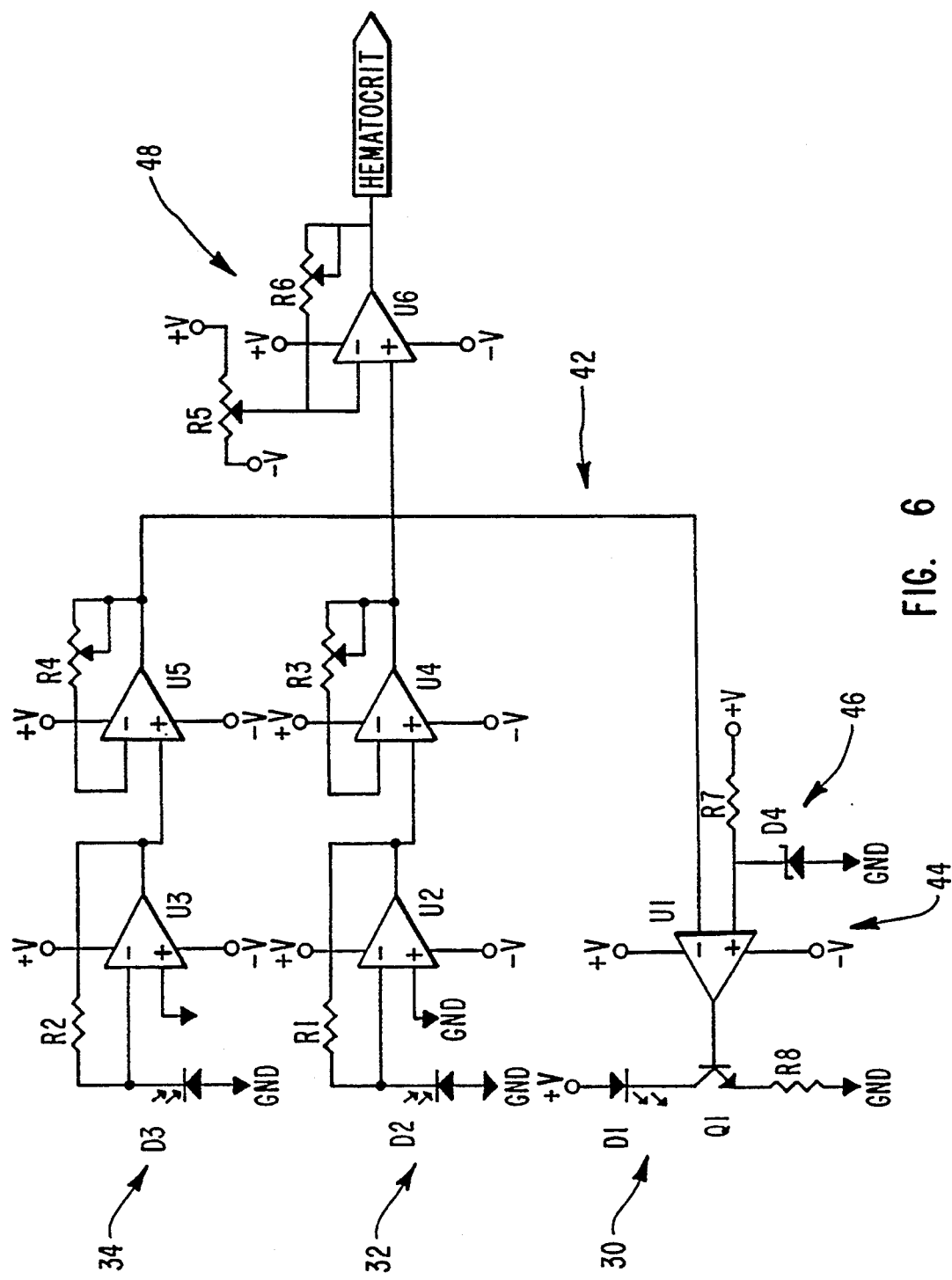
FIG. 6 is a schematic representation of "back-scatter" geometry.
Figure 7:
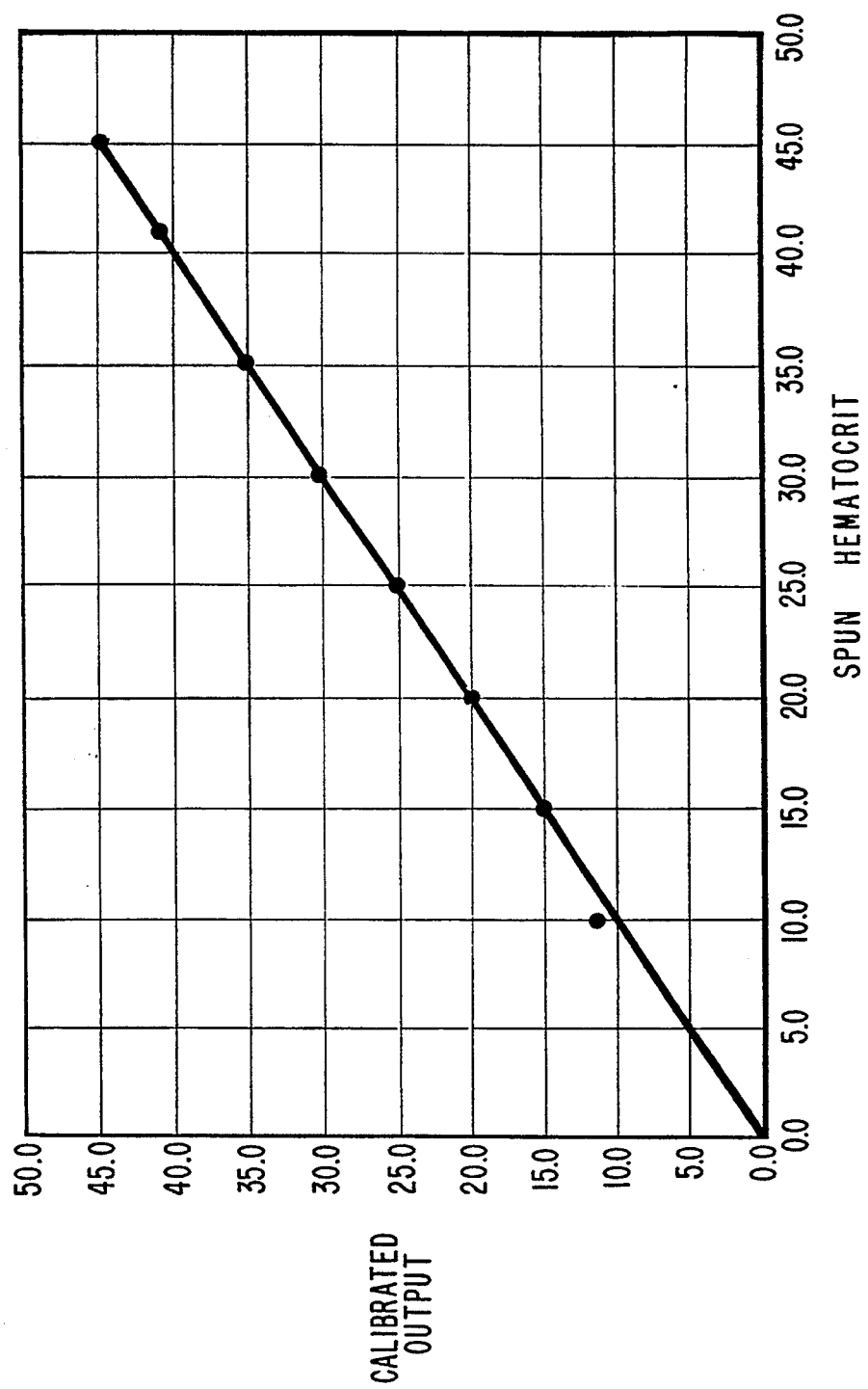
FIG. 7 is a graph of linearity found using the "back-scatter" geometry.

FIG. 6 illustrates the linearity of the output signals of the "back-scatter" geometry. As can be seen from the graph of FIG. 7, with the device of the present invention, complex computer manipulations are again not necessary to form the output signals into a linear hematocrit reading. Calibration, however, converts the signals into more familiar and usable terms. FIG. 7 illustrates the calibrated output signals.

It is within the scope of the present invention for the light emitting diode and the light detecting diodes to be arranged either directly against the blood sample itself, or separated from the bloodstream by a clear window. Although it has been found that better results are obtained when a window is not used, it is more practical to use a window to separate the blood from the diodes. One reason for this is the expense of the diodes. Without an isolating window, the diodes would be in direct contact with the blood and would have to be constantly replaced due to contamination. Another reason is that most applications of the hematocrit sensor will be in extracorporeal circuits, where the clear window may already be present. FIGS. 1 and 4 illustrate use of a window 52 separating the diodes from the blood stream 12.

Figure 5:
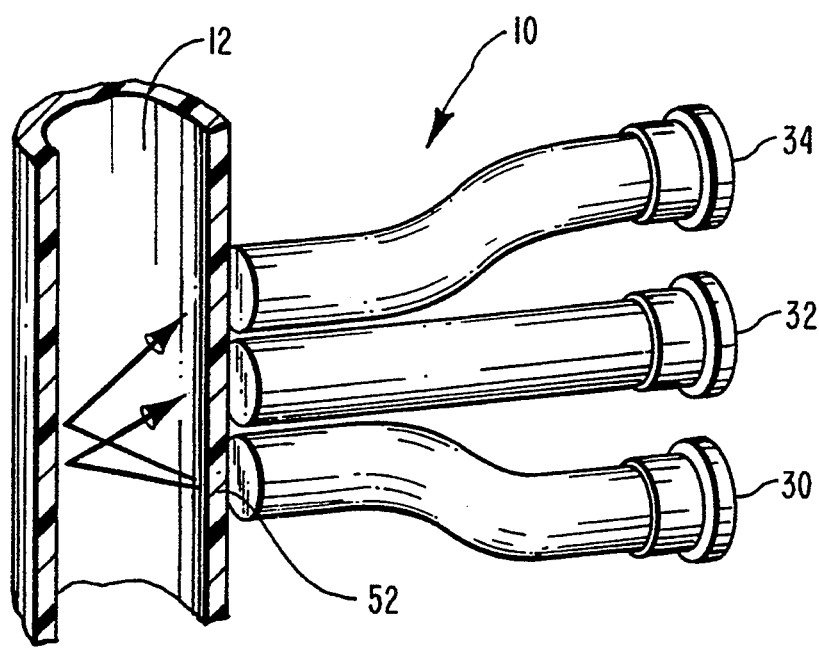
FIG. 5 is a perspective view of the preferred embodiment of the present invention representative of "back-scatter" geometry.

It is also within the scope of the present invention to employ conveying means, in communication with the light emitting means and the light detecting means, for transmitting light from the light emitting means to the blood and to the light detecting means along first and second paths. The first conveying means is in communication with the first light emitting means and transmits light from the light emitting means to the blood. The second conveying means is in communication with the first light detecting means and transmits light to the first light detecting means through the blood along the first path. The third conveying means is in communication with the second light detecting means and transmits light to the second light detecting means through the blood along the second path. The preferred conveying means is illustrated in FIG. 5 as first, second, and third plastic fibers, 54, 56, and 58 respectively. It should be appreciated that glass fibers may also be used within the scope of the present invention.

In the preferred embodiment, one millimeter diameter fibers are placed sided by side next to a blood sample. The light emitting means and the light detecting means are placed on the outer ends of the fibers, and the free ends of the fibers are then placed against the window of the blood stream. As these fibers are one millimeter in diameter, the measurement taken center to center would be two millimeters to the long second path versus one millimeter to the short first path.

In FIG. 5, LED 30 is illustrated as positioned against the end of first fiber 54. Short path diode 32 is positioned against the end of second fiber 56. Long path diode 34 is positioned against the end of third fiber 58. Although the preferred embodiment employs the use of plastic fibers, glass fibers or no fibers at all, may also be used.

For example, FIG. 1 illustrates the first diode 18 and second diode 20 directly against the window 38 of blood stream 12. However, it is possible to add glass or plastic fibers to the embodiment and the embodiment would still perform within the scope of the present invention.

Further, the hematocrit measuring device of the present invention also effectively operates when the light source is pulsed. Pulsing neither adds to nor detracts from the methodology described.

A novel method for measuring the hematocrit of blood using the hematocrit sensor of the present invention is also disclosed. The first step of the novel method comprises positioning a light emitting device so as to emit light into a blood sample. The second step is to energize the light emitting device such that light is emitted through the blood sample.

Next, a first light detecting device is positioned such that it receives light emitted from the light emitting device into the blood along a first path, and a second light detecting device alongside the blood sample such that it also receives light emitted from the light emitting device into the blood. The light emitting device, the first light detecting device and the second light detecting device are all positioned in a predetermined geometric relationship, whereby the second path is longer than the first path.

A feedback circuit is then provided for monitoring the second light detecting device, and regulating the amount of light received by the second light detecting device so that it remains at a constant value. This amount of light may be amplified and sent through the feedback circuit to a regulation circuit where it is compared to a constant reference source. The drive current to the light emitting device is then automatically adjusted so that the value of the amount of light received by the second light detecting device matches the reference value. This thereby also regulates the amount of light emitted by the light emitting device.

The final step comprises amplifying the light received by the first light detecting device and feeding the amplified light to a standard offset and gain calibration amplifier in order to generate an output signal of the first light detecting device which will be a linear representation familiar units of the hematocrit of blood in the blood sample. By this novel method, a linear hematocrit reading is obtained without the need for complex equations processed by a microcomputer.

Another important aspect of the hematocrit sensor of the present invention is its possible use with a plasma separator apparatus such as used in an autotransfusion system. Typical autotransfusion systems in the prior art do not have the capability to constantly monitor and maintain the hematocrit levels of the blood as they process the blood for reinfusion into a patient.

Figure 8:
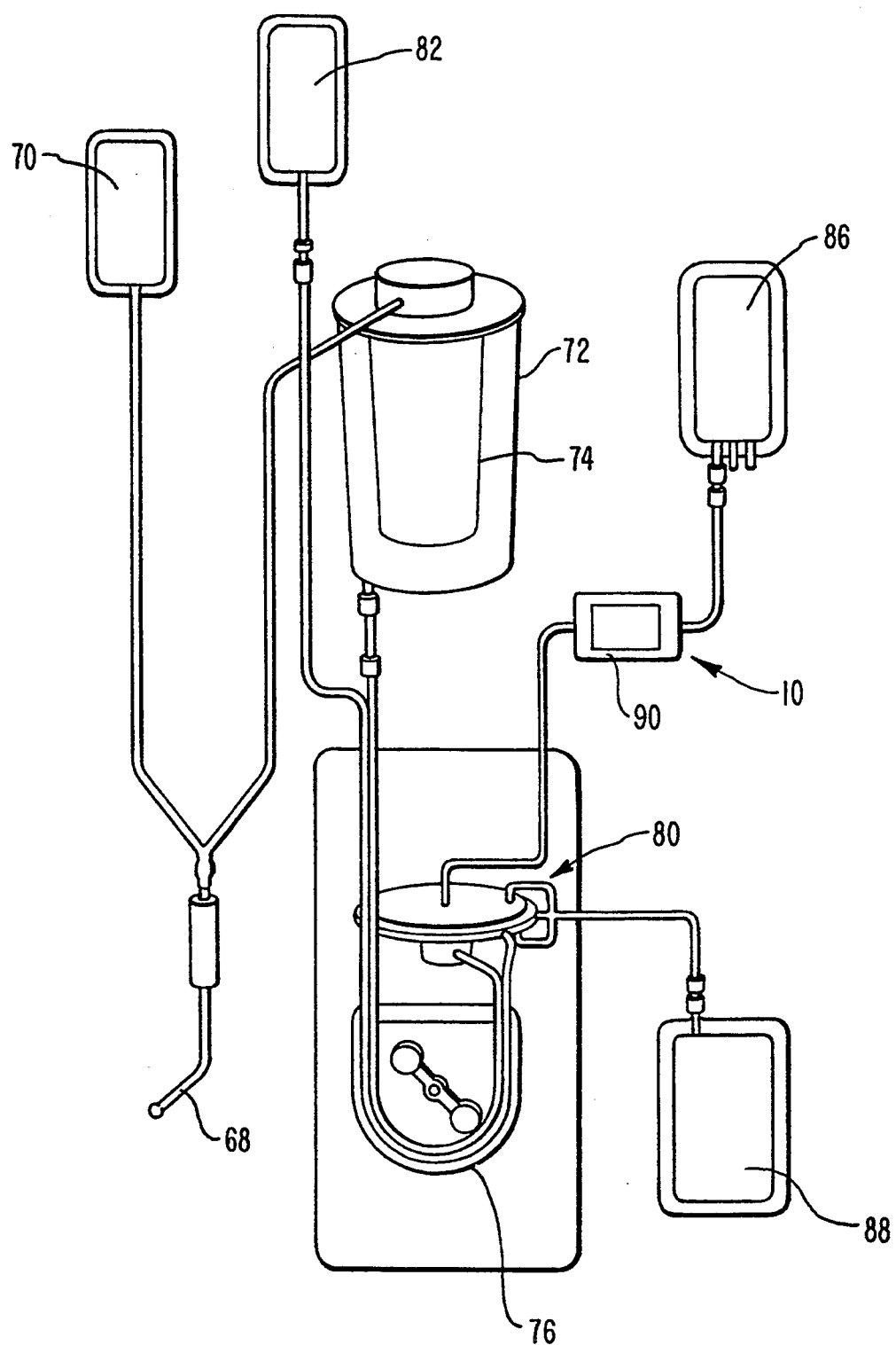
FIG. 8 is a perspective view of an autotransfusion system wherein a hematocrit sensor is attached.

Use of the novel hematocrit sensor with a plasma separator apparatus of an autotransfusion system will be described below, with reference to FIG. 8. Having the hematocrit sensor 10 attached to the autotransfusion system of FIG. 8, identified generally by reference numeral 66, allows automatic monitoring and adjustment of the autotransfusion system. It should be realized that although a particular autotransfusion system is herein described, use of the device of the present invention is not limited to this particular autotransfusion system. Any comparable plasma separator system may be used.

Autotransfusion system 66 is configured for use in recovering blood from a surgical site, so that the blood can be cleaned and returned to the patient. A sucker 68 is used to aspirate blood from a surgical site. A source of anticoagulant 70 is coupled to sucker 68 so that mixing of anticoagulant occurs quickly, thereby minimizing formation of blood clots. Aspirated blood and anticoagulant are drawn into a conventional blood collection reservoir 72, which includes a filter 74 having a pore size which will remove large particles such as blood clots, pieces of tissue, orthopedic cement, and the like, but which will pass cellular components of blood. Blood collection reservoir 72 also serves to effect defoaming of blood collected therein.

A roller pump 76 is advantageously used to pump blood from collection reservoir 72 into a plasma separator, depicted generally by reference numeral 80. A wash solution, preferably saline, is also pumped into plasma separator 80 from a source 82. The wash solution is mixed with partially cleansed blood by rotors (not shown) within the plasma separator 80 in order to effect more thorough separation of waste components from the cellular components of the blood being processed by the plasma separator. Cleansed blood processed by plasma separator 80 is collected in a blood collection bag 86, and from there it is returned to the patient, typically by conventional gravity infusion. Plasma, anticoagulant, and other waste components of the blood are collected in a waste collection bag 88, which may be discarded. A presently preferred plasma separator is described in U.S. patent application Ser. No. 07/844,232, filed Mar. 2, 1992, which is hereby incorporated by reference.

Before blood is collected in blood collection bag 86, it passes through the area where the hematocrit sensor 10 is located. As can be seen in FIG. 8, the hematocrit sensor 10 is positioned within the sensor head 90 between the outlet of the plasma separator 80 and the blood collection bag 86. Not only is hematocrit sensor 10 physically connected to autotransfusion system 66, but it may also be electronically connected by means of a microprocessor which controls the operating parameters of the autotransfusion system.

After the blood is processed by the system, the blood flows past the hematocrit sensor where the hematocrit level of the blood is measured. If the hematocrit level falls out of a certain range, (again, the preferred range here being about 45–55%), an algorithm programmed into the microprocessor will automatically adjust at least one parameter of the plasma separator apparatus so as to compensate for the too high or too low hematocrit. For example, if the hematocrit level is too low, the microprocessor may, as one option, automatically adjust the speed of rotors within the plasma separator in order to increase agitation of the blood, and separation of plasma and waste from the blood. Another option may be to decrease the rate of pumping blood into the system. With less blood flowing through, performance of the system can increase. Alternatively, if the hematocrit level is too high, a separate action can be automatically taken to compensate for the high level.

Thus, it can be seen that through this process, the blood being reinfused into a patient will always have an appropriate hematocrit level.

It is conceivable that many different algorithms may be programmed into the microprocessor so that a variety of actions will be available to compensate for either a low or high hematocrit level. Additionally, the microprocessor may also be programmed so that if the hematocrit level falls to an unacceptable and uncorrectable level, the system will automatically stop, and an alarm sound so as to alert an operator to examine the system.

This programming ability is an advantage over conventional systems. In conventional systems, there is no way of measuring and automatically controlling the hematocrit level of blood should it be found to be too high or low. An operator must always measure the hematocrit separately, and then must make any needed adjustments manually. Constant supervision is necessary.

With the hematocrit sensor of the present invention, however, the hematocrit level of the blood is constantly monitored, and any necessary adjustments to the autotransfusion system automatically takes place by means of the microprocessor linking the hematocrit sensor and the autotransfusion system. Only when the microprocessor cannot adjust the system enough to correct the too high or low hematocrit, will an operator have to step in and solve the problem.

Figure 9:
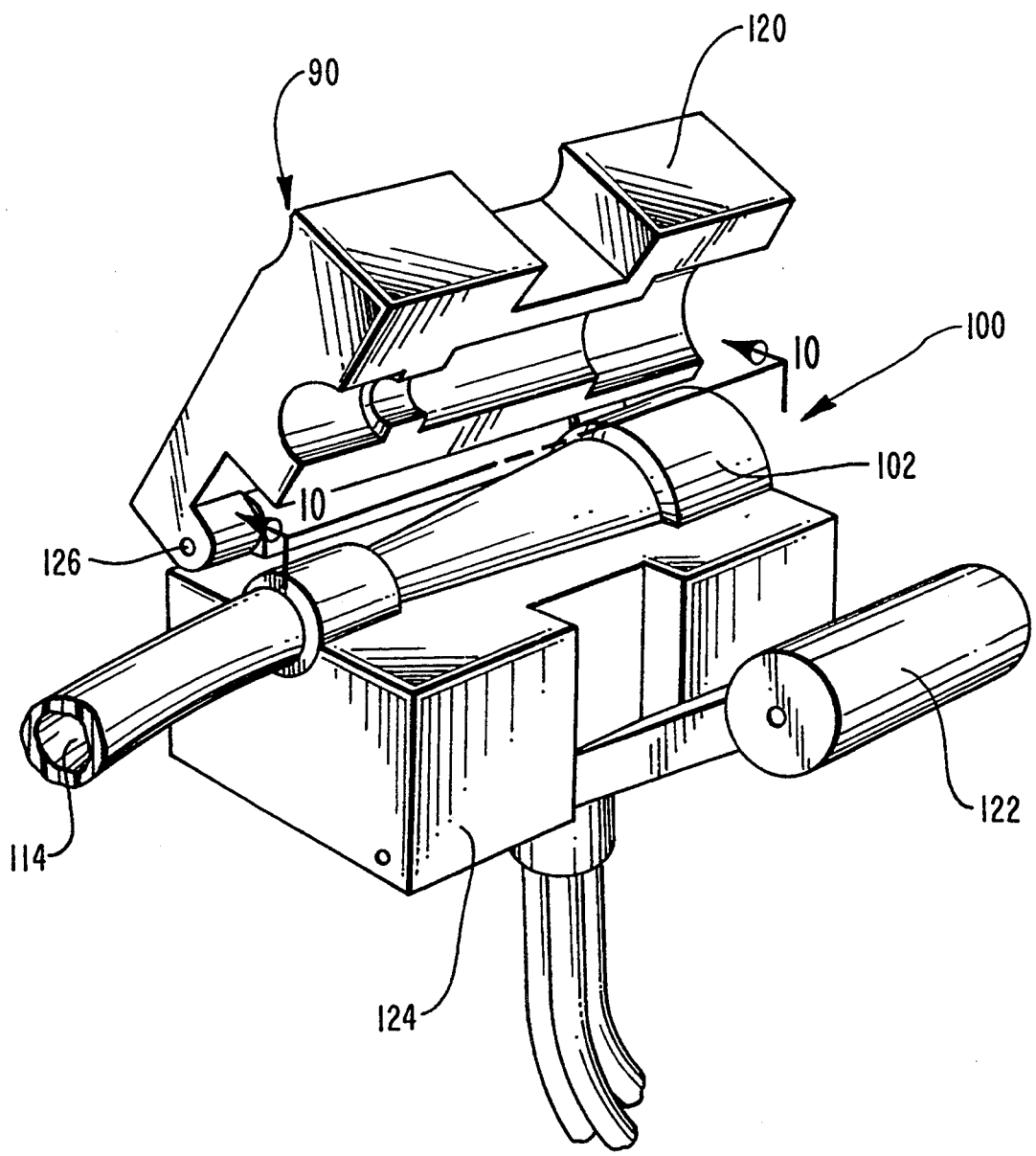
FIG. 9 is a perspective view of an optical connector within the scope of the present invention which provides a window between the flow of blood and the light emitting and light detecting devices.
Figure 10:
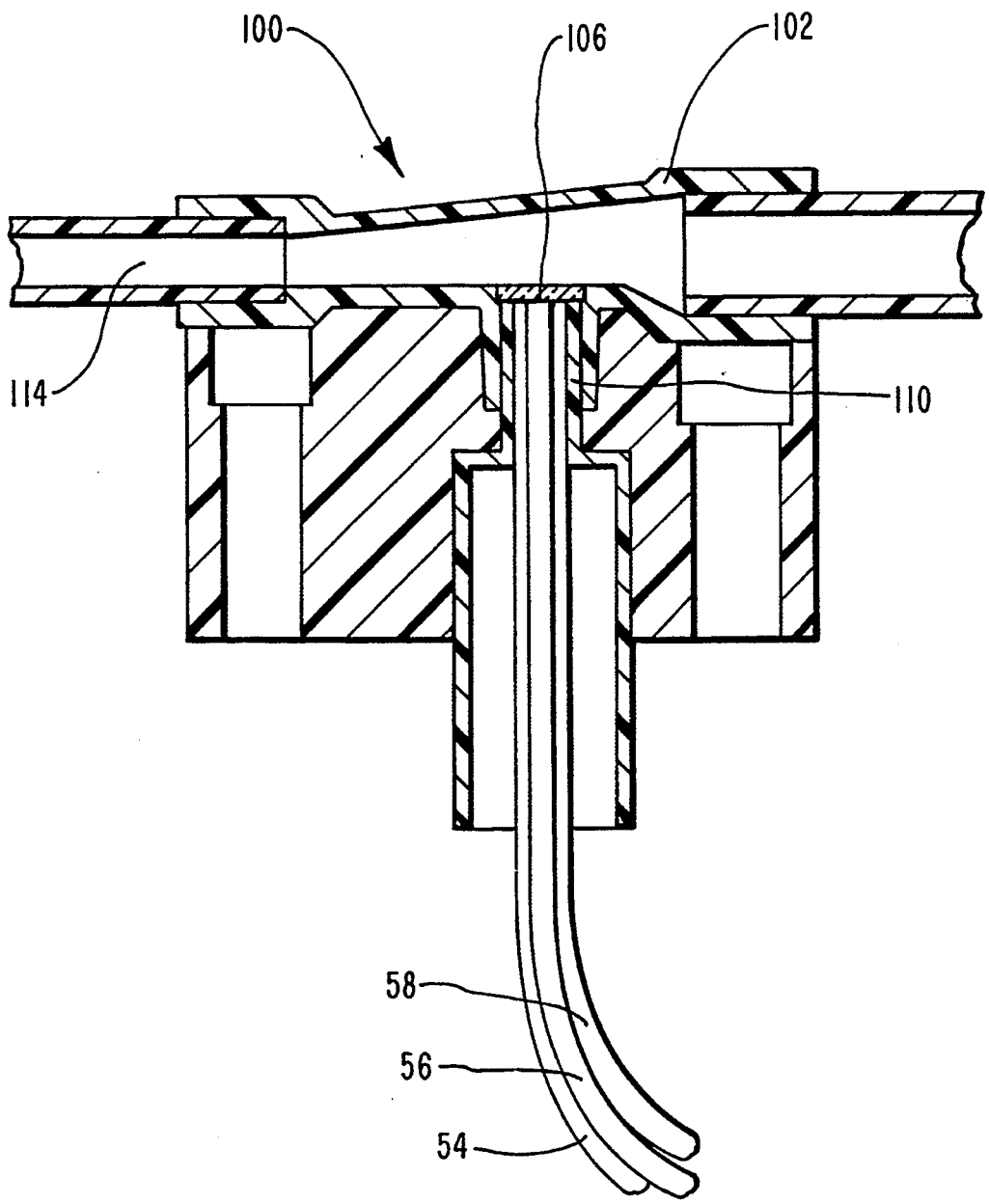
FIG. 10 is a cross-section view of the optical connector of FIG. 9.

A further novel aspect of the present invention is an optical connector used with the hematocrit sensor to separate the components of the hematocrit sensor from direct contact with the blood. The optical connector is illustrated in FIGS. 9 and 10 and labelled 100. Optical connector 100 is comprised of a generally hollow member 102 adapted to receive a blood sample therein with respect to which hematocrit is to be measured. An optically clear flexible optical window 106 is positioned on the generally hollow member 102. Through optical window 106, the blood sample within the generally hollow member 102 may be visually accessed for measurement of its hematocrit. A support 110 for securing the optical fibers to the generally hollow member may extend from the flexible optical window 106 substantially perpendicularly from the generally hollow member 102. As seen in FIGS. 9 and 10 fibers 54, 56 and 58 are secured within support 110 against flexible optical window 106.

Optical window 106 should be completely free of optical defects. The presently preferred material for optical window 106 is a PVC resin. However, any material which is flexible and provides optical clarity is within the scope of the present invention.

As can be seen in FIG. 9, optical connector 100 is placed within the sensor head 90 of hematocrit sensor 10, and the generally hollow member 102 is connected to a blood flow channel 114. As the generally hollow member 102 is connected to blood flow channel 114, flexible optical window 106 is positioned over fibers 54, 56, and 58. By this positioning of the flexible optical window tube 102 over fibers 54, 56, and 58, flexible optical window 106 is pressed against fibers 54, 56, and 58. As optical window 106 is flexible, it forms around and presses firmly against the fibers, thus securing the fibers firmly in place so as to provide visual access to the blood sample while protecting the fibers from direct contact with the blood. With use of the optical connector 100, the fibers never directly contact the blood, and so do not have to be replaced with each use.

When fibers 54, 56 and 58 are pressed against flexible optical window 106, flexible optical window 106 conforms its shape to the ends of the fibers so that the flexible optical window 106 rests against fibers 54, 56 and 58 tightly. Generally, because of tolerances, it is difficult to align fibers 54, 56 and 58 so that the end of each fiber terminates against the optical window. To compensate for this tolerance variation, flexible optical window 106 is flexible enough so that the fibers will mate tightly with the optical window and allow detection of the blood sample through the flexible optical window 106 while preventing contact between the blood and the detectors.

In one embodiment, once the fibers are positioned into support 110, they are glued into place.

Optical connector 100 is a disposable component of the hematocrit sensor system. Once used, it may be removed from sensor head 90 and thrown away. Although it is substantially cylindrical in the preferred embodiment, other shapes are also within the scope of the present invention.

In FIG. 9, it can be seen that optical connector 100 lies inside of sensor head 90. Sensor head 90 is comprised of a lid 120 and a bottom half 124 connected on one side by a hinge 126. When lid 120 of sensor head 90 is opened, optical connector 100 may be placed inside. A locking arm 122 used to allow access to the inside of sensor head 90 by engaging lid 120 to bottom half 124, or disengaging lid 120 from bottom half 124, is connected to bottom half 124 of sensor head 90. Locking arm 122 pivots upwards around its point of connection with bottom half 124 of sensor head 90 and engages with lid 120, thus securing lid 120 to bottom half 124 and thereby placing sensor head 90 into a closed position. When locking arm 122 is pivoted downward, it disengages with lid 120, and allows lid 120 to be lifted, thereby placing sensor head 90 into an opened position wherein optical connector 100 can be placed inside, or withdrawn.

Another important aspect of the present invention which is disclosed herein is the novel method for automatically controlling the operation of an autotransfusion system by using hematocrit measurement to control parameters of a plasma separator apparatus. The first step of this method comprises attaching a hematocrit sensor to a plasma separator apparatus wherein cellular components of blood, red blood cells, white blood cells, and platelets, are separated from such waste components as plasma, anticoagulant, toxins, and other relatively small molecules. Once attached, the hematocrit sensor can then constantly monitor the hematocrit level in the blood during operation of the separator apparatus, so that the operation of the separator apparatus can be adjusted in order to keep the hematocrit level within a desired range. Thus, with the hematocrit sensor of the present invention, the operator of a plasma separator apparatus can know when adjustments to the operating parameters of the plasma separator device are necessary in order to obtain high quality blood, and can take action immediately after being notified by readings of the hematocrit sensor.

The hematocrit sensor of the present invention may be used with many different types of autotransfusion systems. In one particular system, however, blood is pumped through a plasma separator apparatus, where rotating means within the apparatus for producing movement of cellular components of blood causes turbulence. This thereby increases the filtration of waste components. Through readings from the hematocrit sensor of the present invention, the operator of the plasma separator apparatus would be able to know whether the speed of the rotor means should be increased or decreased in order to obtain the right amount of filtration necessary to produce a hematocrit level within a desired range.

It can be appreciated that the hematocrit sensor may not only be physically coupled with the autotransfusion system, but it may also be electronically joined to the plasma separator apparatus of the autotransfusion system. One possible way would be through connection by a microprocessor. The microprocessor could function to process measurements obtained by the hematocrit sensor. If the measurements do not fall within a predetermined acceptable range, the microprocessor can then automatically adjust at least one operating parameter of the plasma separator apparatus in order to bring the hematocrit back to the desired range. Various algorithms can be programmed into the microprocessor such that each hematocrit reading automatically produces a different and appropriate response from the plasma separator apparatus.

Other ways for the hematocrit sensor to be electronically linked to the plasma separator apparatus are by using discrete circuitry, or by using a limit switch. The regulation circuit of the present invention can be used to hold the motor of the apparatus constant. The inherent linearity of the signal outputs of the present device is used to control the circuits and switches.

It will be readily appreciated that the hematocrit sensor of the present invention may be used with many types of different systems, as well as with other apparatus such as heart and lung machines.

It should also be noted that one use of the hematocrit sensor may be to detect air in the blood. If the hematocrit is low, during conditions when there should be large quantity of blood cells, it may be deduced that air is present and the machine can be stopped. This capability can be useful, for example, when the blood is in a bag which is gravity connected to a patient. It is important not to force air into the patient.

Further, the hematocrit sensor may be used with a autotransfusion system to indicate the beginning or ending of each autotransfusion cycle. If the hematocrit measurement of blood before and after being processed by an autotransfusion system is known, then by monitoring the hematocrit measurements as registered by the hematocrit sensor, an operator could identify the beginning and end of each cleansing cycle.

The present invention may be embodied in other specific forms without departing from its spirit or essential characteristics. The described embodiments are to be considered in all respects only as illustrative and not restrictive, and the scope of the invention is indicated by the appended claims rather than by the foregoing description. All changes which come within the meaning and range of equivalency of the claims are to be embraced within their scope.

What is claimed and desired to be secured by United States Patent is:

1. An apparatus for measuring the hematocrit of blood comprising
    light emitting means for emitting light into a blood sample;
    first light detecting means for detecting light emitted from the light emitting means, said first light detecting means positioned to receive light emitted from the light emitting means into the blood sample along a first path from the light emitting means, through the blood sample, to the first light detecting means, the first light detecting means outputting a signal corresponding to the amount of light detected;
    second light detecting means for detecting light emitted from the light emitting means, said second light detecting means being positioned to receive light emitted from the light emitting means into the blood sample, such that light emitted from the light emitting means must travel farther to reach the second light detecting means than to reach the first light detecting means, thereby forming a second path from the light emitting means, through the blood sample, to the second light detecting means which is longer than the first path from the light emitting means to the first light detecting means, the second light detecting means outputting a signal corresponding to the amount of light detected; and
    light intensity regulating means for regulating the intensity of light emitted by the light emitting means such that the received light on one of the paths remains at a constant value.

2. An apparatus for measuring the hematocrit of blood as defined in claim 1, wherein the light emitting means comprises an infrared light emitting diode.

3. An apparatus for measuring the hematocrit of blood as defined in claim 1, wherein the light emitting means comprises an infrared laser.

4. An apparatus for measuring the hematocrit of blood as defined in claim 2, wherein the infrared light emitting diode emits light at approximately 805 nanometers.

5. An apparatus for measuring the hematocrit of blood as defined in claim 1, wherein at least one of the light detecting means comprises a PIN diode.

6. An apparatus for measuring the hematocrit of blood as defined in claim 1, further comprising amplifying means for providing an amplified signal which is a linear representation of the hematocrit of blood in the blood sample.

7. An apparatus for measuring the hematocrit of blood as defined in claim 1, wherein at least one of the light detecting means comprises a photodetector.

8. An apparatus for measuring the hematocrit of blood as defined in claim 1, further comprising:
    first conveying means, in communication with the light emitting means, for transmitting light from the light emitting means to the blood;
    second conveying means, in communication with the first light detecting means, for transmitting light passing through the blood to the first light detecting means along the first path; and
    third conveying means, in communication with the second light detecting means, for transmitting light passing through the blood to the second light detecting means along the second path.

9. An apparatus for measuring the hematocrit of blood as defined in claim 8, wherein the conveying means comprises glass fibers.

10. An apparatus for measuring the hematocrit of blood as defined in claim 8, wherein the conveying means comprises plastic fibers.

11. An apparatus for measuring the hematocrit of blood as defined in claim 1, further comprising an optical connector, said optical connector comprising a generally hollow member adapted to receive therein the blood sample with respect to which hematocrit is to be measured, and an optically clear flexible optical window positioned on the generally hollow member through which blood can be monitored.

12. An apparatus for measuring the hematocrit of blood as defined in claim 11, further comprising a support extending from the flexible optical window substantially perpendicularly from the hollow member, for securing to the hollow member the light emitting and light detecting means, thereby allowing the light emitting and light detecting means access to the blood sample without direct contact with the blood sample.

13. An apparatus for measuring the hematocrit of blood as defined in claim 11, wherein the flexible optical window comprises a polyvinylchloride resin material.

14. An apparatus for measuring the hematocrit of blood as defined in claim 11, wherein the flexible optical window comprises an optically clear material.

15. An apparatus for measuring the hematocrit of blood comprising:
- light emitting means for emitting light into a blood sample;
- first light detecting means the detecting light emitted from the light emitting means, said first light detecting means positioned to receive light emitted from the light emitting means into the blood sample along a first path from the light emitting means, through the blood sample. to the first light detecting means, said first light detecting means outputting a signal corresponding to the amount of light detected;
- second light detecting means for detecting light emitted from the light emitting means. said second light detecting means being positioned to receive light emitted from the light emitting means into the blood sample, such that light emitted from the light emitting means must travel farther to reach the second light detecting means than to reach the first light detecting means, thereby forming a second path from the light emitting means, through the blood sample, to the second light detecting means which is longer than the first path from the light emitting means to the first light detecting means, the second light detecting means outputting a signal corresponding to the amount of light detected;
- first conveying means, in communication with the light emitting means, for transmitting light from the light emitting means to the blood;
- second conveying means, in communication with the near detecting means, for transmitting to the first light detecting means light passing through the blood along the first path;
- third conveying means, in communication with the far detecting means, for transmitting to the second light detecting means light passing through the blood along the second path; and
- light intensity regulating means for regulating the intensity of light emitted by the light emitting means such that the received light on one of the paths remains at a constant value.

16. An apparatus for measuring the hematocrit of blood as defined in claim 15, wherein the light emitting means comprises an infrared light emitting diode.

17. An apparatus for measuring the hematocrit of blood as defined in claim 15, wherein the light detecting means comprises a photodiode.

18. An apparatus for measuring the hematocrit of blood as defined in claim 15, wherein the conveying means comprises glass fibers.

19. An apparatus for measuring the hematocrit of blood as defined in claim 15, wherein the conveying means comprises plastic fibers.

20. An apparatus for measuring the hematocrit of blood as defined in claim 15, further comprising amplifying means for performing offset and gain calibration of the signals output from the first and second light detecting means so as to provide an amplification signal which is a linear representation of the hematocrit of blood in the blood sample.

21. An optical connector for use with a hematocrit sensor comprising:
- a generally hollow member adapted to receive a blood sample therein with respect to which hematocrit is to be measured; and
- an optically clear flexible optical window positioned on the generally hollow member, and through which the blood sample within the generally hollow member may be visually accessed for measurement of its hematocrit;
- wherein the optical connector presses firmly into the flexible optical window to permit a substantially tight fitting contact.

22. An optical connector as defined in claim 21, wherein the flexible optical window comprises a polyvinylchloride resin material.

23. An apparatus for measuring the hematocrit of blood as defined in claim 21, further comprising a support extending from the flexible optical window substantially perpendicularly from the generally hollow member for securing to the hollow member a hematocrit sensor so as to allow measurement of the hematocrit of the blood sample within the generally hollow member.

24. An apparatus for regulating the operation of a plasma separator apparatus to keep the hematocrit measurement of blood output therefrom within a predetermined range, comprising:
- a plasma separator apparatus for removing unwanted waste components from the blood in order to cleanse the blood; and
- monitoring means for measuring the hematocrit of the cleansed blood outputted from the plasma separator apparatus, and for thereafter automatically regulating operating parameters of the plasma separator apparatus so as to maintain a hematocrit of the blood within a predetermined range;
- wherein the monitoring means for automatically regulating operating parameters of the plasma separator apparatus comprises a hematocrit sensor for measuring the hematocrit of blood, interconnected with the plasma separator apparatus by a microcomputer, said hematocrit sensor comprising light emitting means for emitting light into a blood sample, first light detecting means for detecting light emitted from the light emitting means, said first light detecting means positioned to receive light emitted from the light emitting means, through the blood sample, along a first path, and the first light detecting means outputting a signal corresponding to the amount of light detected, second light detecting means detecting light emitted from the light emitting means, said second light detecting means being positioned to receive light emitted from the light emitting means, through the blood sample, along a second path, such that light emitted from the light emitting means must travel farther to reach the second detecting means than to reach the first light detecting means, thereby forming a second path from the light emitting means to the second light detecting means which is longer than the first path from the light emitting means to the first light detecting means, and light intensity regulating means for regulating the intensity of light emitted by the light emitting means such that the received light in one of the paths remains at a constant value.

25. An apparatus for regulating the operation of a plasma separator apparatus to keep the measurement of blood output therefrom within a predetermined range, comprising:

a plasma separator apparatus removing unwanted waste components from the blood in order to cleanse the blood; and monitoring means for measuring the hematocrit of the cleansed blood outputted from the plasma separator apparatus, and for thereafter automatically regulating operating parameters of the plasma separator apparatus so as to maintain a hematocrit of the blood within a predetermined range;

wherein the monitoring means for automatically regulating operating parameters of the plasma separator apparatus comprises a hematocrit sensor for measuring the hematocrit of blood, interconnected with the plasma separator apparatus by limit switches, said hematocrit sensor comprising light emitting means for emitting light into a blood sample, first light detecting means for detecting light emitted from the light emitting means, said first light detecting means positioned to receive light emitted from the light emitting means, through the blood sample, along a first path, and the first light detecting memos outputting a signal corresponding to the amount of light detected, second light detecting means for detecting light emitted from the light emitting means, said second light detecting means being positioned to receive light emitted from the light emitting mean, through the blood sample, along a second path, such that light from the light emitting means must travel further to reach the second detecting means than to reach the first light detecting means, thereby forming a second path from the light emitting means to the second light detecting means which is longer than the first path from the light emitting means to the first light detecting means, and light intensity regulating means for regulating the intensity of light emitted by the light emitting means such that the received light on one of the paths remains at a constant value.

* * * * *